United States Patent
Kawano et al.

(10) Patent No.: US 9,022,944 B2
(45) Date of Patent: May 5, 2015

(54) ELECTRONIC SPHYGMOMANOMETER

(75) Inventors: Atsushi Kawano, Takarazuka (JP); Yukiya Sawanoi, Nara (JP)

(73) Assignee: Omron Healthcare Co., Ltd., Kyoto (JP)

( * ) Notice: Subject to any disclaimer, the term of this patent is extended or adjusted under 35 U.S.C. 154(b) by 502 days.

(21) Appl. No.: 13/463,973

(22) Filed: May 4, 2012

(65) Prior Publication Data

US 2012/0215119 A1    Aug. 23, 2012

Related U.S. Application Data

(63) Continuation of application No. PCT/JP2010/069471, filed on Nov. 2, 2010.

(30) Foreign Application Priority Data

Nov. 4, 2009  (JP) ................................. 2009-252682

(51) Int. Cl.
| | |
|---|---|
| *A61B 5/02* | (2006.01) |
| *A61B 5/022* | (2006.01) |
| *A61B 5/021* | (2006.01) |
| A61B 5/0225 | (2006.01) |
| A61B 5/023 | (2006.01) |

(52) U.S. Cl.
CPC ......... *A61B 5/02233* (2013.01); *A61B 5/02141* (2013.01); *A61B 5/0225* (2013.01); *A61B 5/023* (2013.01); *A61B 2560/0276* (2013.01)

(58) Field of Classification Search
CPC .. A61B 5/02141; A61B 5/022; A61B 5/0225; A61B 5/02255
USPC ......................................................... 600/490
See application file for complete search history.

(56) References Cited

U.S. PATENT DOCUMENTS 4,953,557 A * 9/1990 Frankenreiter et al. ....... 600/493
2006/0064023 A1* 3/2006 Yang et al. .................... 600/490

FOREIGN PATENT DOCUMENTS

| JP | 02-019133 A | 1/1990 |
|---|---|---|
| JP | 04-193257 A | 7/1992 |
| JP | 05-023310 A | 2/1993 |

(Continued)

OTHER PUBLICATIONS

Patent Abstracts of Japan, Publication No. 02-019133, publication date Jan. 23, 1990 (1 page).

(Continued)

*Primary Examiner* — Etsub Berhanu
(74) *Attorney, Agent, or Firm* — Osha Liang LLP

(57) ABSTRACT

An electronic sphygmomanometer includes a cuff, a tank that stores a prescribed amount of fluid, a pressure adjusting unit that adjusts pressurization of the cuff or the tank by supplying or discharging the fluid, a pressure detector that detects a pressure in the cuff or a pressure in the tank based on pressure information output from a pressure sensor, a blood pressure calculating unit that calculates a blood pressure value based on a change in the pressure in the cuff detected by the pressure detector, an abnormality detector, and a first channel through to the pressure adjusting unit and the pressure detector and that has one of the tank and the cuff selectively connected thereto. The abnormality detector detects whether the pressure sensor is abnormal in a state where the tank is connected to the first channel and the fluid is supplied to the tank.

12 Claims, 17 Drawing Sheets

(56) References Cited

FOREIGN PATENT DOCUMENTS

| | | |
|---|---|---|
| JP | 07-178065 A | 7/1995 |
| JP | 2010-057817 A | 3/2010 |
| WO | WO 2009093515 A1 * | 7/2009 |

OTHER PUBLICATIONS

Patent Abstracts of Japan, Publication No. 05-023310, publication date Feb. 2, 1993 (1 page).
Patent Abstracts of Japan, Publication No. 04-193257, publication date Jul. 13, 1992 (1 page).
Patent Abstracts of Japan, Publication No. 07-178065, publication date Jul. 18, 1995 (1 page).
Patent Abstracts of Japan, Publication No. 2010-057817, publication date Mar. 18, 2010 (1 page).
International Search Report issued in PCT/JP2010/069471 mailed on Dec. 7, 2010, with English translation thereof, 4 pages.

* cited by examiner

| ID | User | Measurement date/time | Blood pressure value/Pulse rate | Sensor |
|---|---|---|---|---|
| 1 | A | yy/mm/dd hh:mm1 | SYS1 , DIA1 , PLS1 | OK |
| 2 | B | yy/mm/dd hh:mm2 | SYS2 , DIA2 , PLS2 | OK ← Date of previous sensor inspection |
| 3 | A | yy/mm/dd hh:mm3 | SYS3 , DIA3 , PLS3 | OK |
| 4 | A | yy/mm/dd hh:mm4 | SYS4 , DIA4 , PLS4 | OK |

D1, D2, D3, D4, D5 — 43

⇩

(B)

| ID | User | Measurement date/time | Blood pressure value/Pulse rate | Sensor |
|---|---|---|---|---|
| 1 | A | yy/mm/dd hh:mm1 | SYS1 , DIA1 , PLS1 | OK |
| 2 | B | yy/mm/dd hh:mm2 | SYS2 , DIA2 , PLS2 | OK ← Date of previous sensor inspection |
| 3 | A | yy/mm/dd hh:mm3 | SYS3 , DIA3 , PLS3 | NG |
| 4 | A | yy/mm/dd hh:mm4 | SYS4 , DIA4 , PLS4 | NG |
| 5 | B | yy/mm/dd hh:mm5 | SYS5 , DIA5 , PLS5 | NG ← Date of current sensor inspection |

ELECTRONIC SPHYGMOMANOMETER

TECHNICAL FIELD

This invention relates to an electronic sphygmomanometer, and more particularly to an electronic sphygmomanometer that is able to obtain high measurement accuracy.

BACKGROUND ART

Electronic sphygmomanometers that measure blood pressure using arterial pressure information detected from the upper arm, wrist or finger are in widespread use, and accurate measurement of blood pressure is desired.

Causes of fluctuation in blood pressure measurements can be roughly divided into fluctuation attributable to the person who is being measured (blood pressure fluctuation or error due to the measurement method) or fluctuation attributable to the device (abnormality of pressure sensor). The latter cause, in particular, is avoidable by periodically calibrating the device.

However, sphygmomanometers purchased for household use are generally not calibrated, except under specific circumstances such as when they malfunction. Thus, even if, for example, the output of the pressure sensor, which is vital in measuring blood pressure, is outside a stipulated tolerance range, there is no way of knowing this, and it is uncertain whether the measured blood pressure value is correct or not. Thus, in the case where there is a large difference between the measured blood pressure value and the normal blood pressure value, it is uncertain whether the blood pressure itself has fluctuated or whether the measured blood pressure value has fluctuated due to a pressure sensor error, giving the person being measured cause for concern.

Also, some sphygmomanometers for use in medical facilities are equipped with two pressure sensors, and monitor pressure based on the output of these pressure sensors. However, the functions of the two pressure sensors are used for different purposes. In other words, blood pressure is calculated with cuff pressure information obtained with one of the pressure sensors, and abnormality detection is performed based on the output of the other pressure sensor. Specifically, when the detected pressure value of the other pressure sensor greatly exceeds 300 mm Hg, for example, an abnormality is detected. In this case, safety is ensured by stopping the pump and opening the valve. This ensuring of safety is a requirement of the medical standard IEC 60601-2-30.

One example of a sphygmomanometer that is equipped with a plurality of pressure sensors and monitors operation failure of the pressure sensors is shown in the Patent Literature 1.

CITATION LIST

Patent Literature

Patent Literature 1: JP 2-19133A

SUMMARY OF INVENTION

With the electronic sphygmomanometer of Patent Literature 1 (JP 2-19133A), malfunction cannot be detected in the case where all of the plurality of pressure sensors mounted therein have malfunctioned. Also, mounting a plurality of pressure sensors increases the cost and size of the device, and hinders the widespread use of sphygmomanometers for household use.

Hence, one or more embodiments of the present invention provide an electronic sphygmomanometer that is able to improve the reliability of measured blood pressure values by detecting abnormality of a pressure sensor.

An electronic sphygmomanometer according to one or more embodiments of the present invention includes a cuff to be mounted on a measurement site, a tank capable of storing a prescribed amount of a fluid, a pressure adjusting unit that adjusts pressurization of the cuff or the tank by supplying or discharging the fluid, a pressure detector including a pressure sensor and for detecting a pressure in the cuff or a pressure in the tank based on pressure information output from the pressure sensor, a blood pressure calculating unit that calculates a blood pressure value based on a change in the pressure in the cuff detected by the pressure detector, an abnormality detector that detects whether the pressure sensor is abnormal, and a first channel through to the pressure adjusting unit and the pressure detector and for having one of the tank and the cuff selectively connected thereto. The abnormality detector detects whether the pressure sensor is abnormal, based on the pressure in the tank detected by the pressure detector in accordance with the pressure information output from the pressure sensor, in a state where the tank is connected to the first channel and the fluid is supplied to the connected tank.

According to one or more embodiments of the present invention, the electronic sphygmomanometer further includes a second channel through to the cuff, and a third channel through to the tank, the abnormality detector includes a channel switching unit that selectively connects one of the second channel and the third channel to the first channel, and the channel switching unit has a switching valve that connects one of the second channel and the third channel to the first channel, in accordance with a provided switching signal.

According to one or more embodiments of the present invention, the channel switching unit has a connecting portion for detachably connecting the second channel to a main body of the electronic sphygmomanometer, and a plug member for blocking off the second channel, the second channel through to the cuff integrally includes the connecting portion, and the connecting portion is a hollow cylinder, with the second channel being connected to the first channel as a result of the connecting portion being mounted on the main body such that the cylinder is inserted into the first channel and the third channel is blocked off by the inserted cylinder, and the third channel being connected to the first channel as a result of the plug member being mounted on the main body in place of the connecting portion.

According to one or more embodiments of the present invention, the pressure adjusting unit includes a pump for sending the fluid at a fixed flow rate per unit time, and supplies the prescribed amount of the fluid to the tank by driving the pump for a fixed time period.

According to one or more embodiments of the present invention, the electronic sphygmomanometer further includes a temperature detector that detects an ambient temperature of the tank, and the prescribed amount is changed in accordance with the temperature detected by the temperature detector.

According to one or more embodiments of the present invention, a result of detection by the abnormality detector is output externally.

According to one or more embodiments of the present invention, the electronic sphygmomanometer further includes a storage unit, and a result of detection by the abnormality detector is stored in the storage unit in association with data indicating the blood pressure value calculated by the blood pressure calculating unit and a time at which the blood pressure value was calculated.

According to one or more embodiments of the present invention, the abnormality detector detects whether the pressure sensor is abnormal, at a time of starting the electronic sphygmomanometer.

According to one or more embodiments of the present invention, the abnormality detector detects whether the pressure sensor is abnormal, at a time of calculating the blood pressure value by the blood pressure calculating unit.

According to one or more embodiments of the present invention, the abnormality detector detects whether the pressure sensor is abnormal, every prescribed time interval.

According to one or more embodiments of the present invention, the abnormality detector detects whether the pressure sensor is abnormal, whenever the blood pressure value calculation by the blood pressure calculating unit is performed a prescribed number of times.

According to one or more embodiments of the present invention, the abnormality detector detects whether the pressure sensor is abnormal, when an instruction is provided from outside.

According to one or more embodiments of the present invention, abnormality of a pressure sensor can be detected with only the main body of an electronic sphygmomanometer, enabling the reliability of measured blood pressure values to be improved.

BRIEF DESCRIPTION OF DRAWINGS

FIG. 5 is a diagram showing exemplary storage content of a memory according to one or more embodiments of the present invention.

DETAILED DESCRIPTION OF INVENTION

Figure 1:
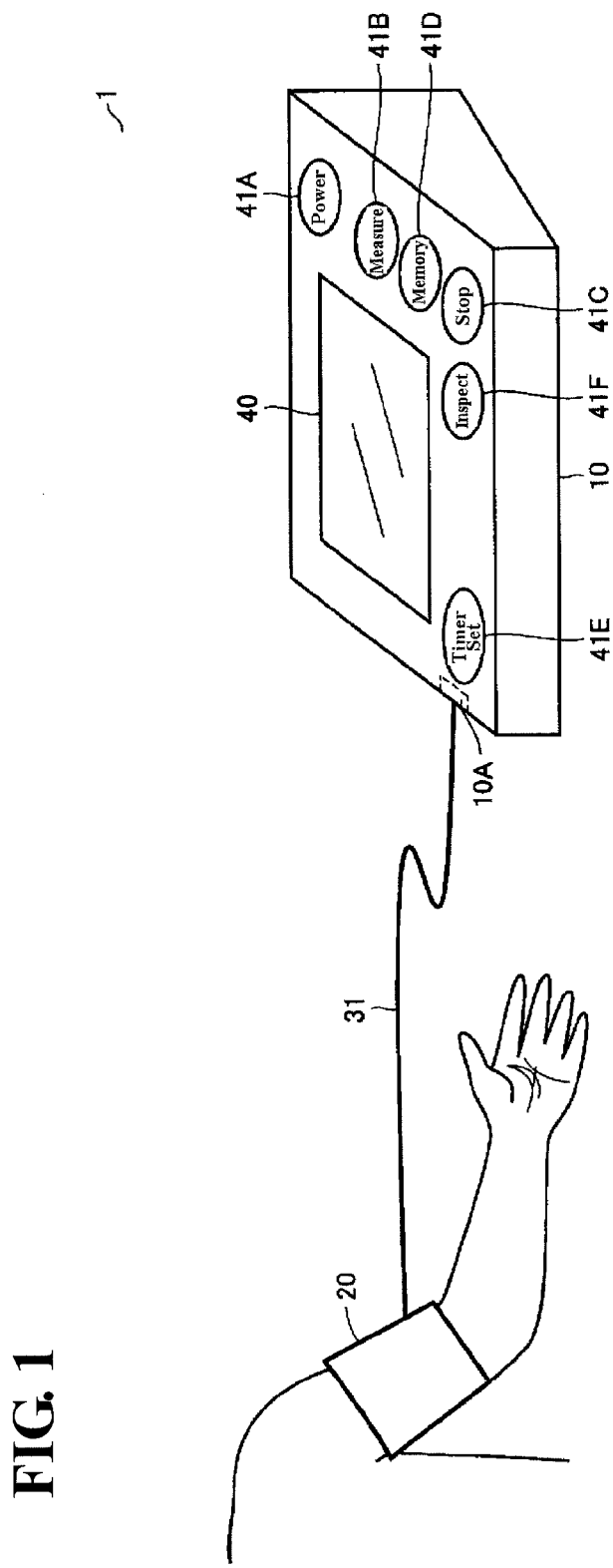
FIG. 1 is an external view of an electronic sphygmomanometer according to one or more embodiments of the present invention.

Hereinafter, embodiments of this invention are described in detail with reference to drawings. Note that in the drawings the same reference signs indicate the same or equivalent portions, and description thereof is not repeated.

In the present embodiment, an electronic sphygmomanometer that calculates blood pressure using an oscillometric method with the upper arm as the measurement site and is equipped with one pressure sensor for measuring blood pressure is described. Note that the method applied in order to calculate blood pressure is not limited to the oscillometric method. Also, the fluid used for inflating/deflating the cuff is given as air.

Figure 2:
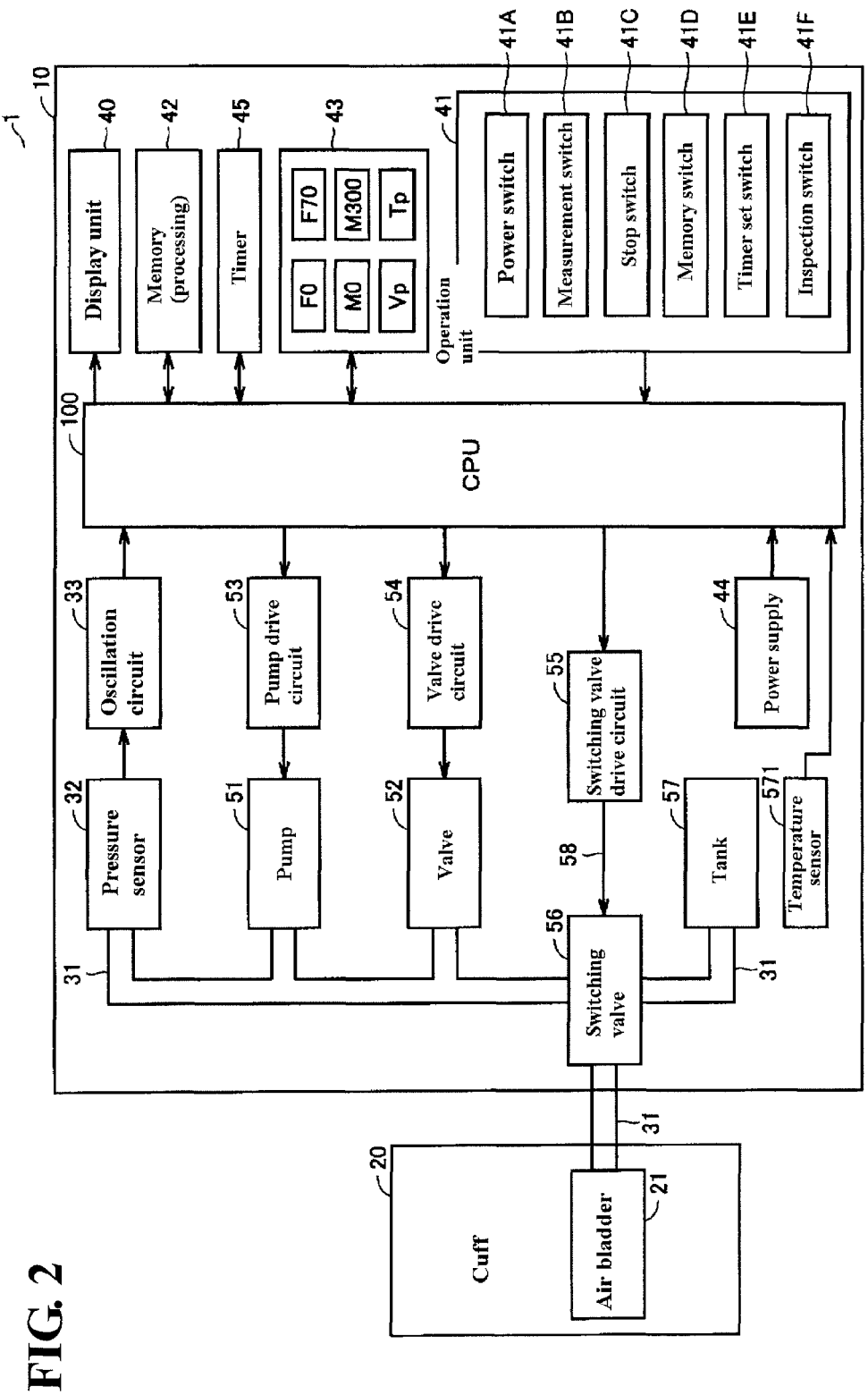
FIG. 2 is a hardware configuration diagram of the electronic sphygmomanometer according to one or more embodiments of the present invention.

The external appearance of the electronic sphygmomanometer 1 according to one or more embodiments of the present invention is shown in FIG. 1, and the hardware configuration of the electronic sphygmomanometer is shown in FIG. 2. Referring to FIG. 1 and FIG. 2, the electronic sphygmomanometer 1 is provided with a main body portion 10 and a cuff 20 that can be wrapped around the upper arm of a person who is being measured. The cuff 20 includes an air bladder 21. The surface of the main body portion 10 has arranged thereon a display unit 40 constituted by liquid crystals or the like, for example, and an operation unit 41 consisting of a plurality of switches for receiving instructions from a user (person being measured).

The main body portion 10, in addition to the display unit 40 and the operation unit 41, includes a CPU (Central Processing Unit) 100 for performing centralized control of the units and various types of arithmetic operations, a processing memory 42 for storing data and programs for causing the CPU 100 to perform prescribed operations, a data storage memory 43, a power supply 44 for supplying power to the units of the main body portion 10, and a timer 45 that clocks the current time and outputs clocked data to the CPU 100.

The operation unit 41 has various switches that are operated by the person being measured. That is, the operation unit 41 has a power switch 41A operated by the person being measured in order to input a power supply ON or OFF instruction, a measurement switch 41B operated in order to input a measurement start instruction, a stop switch 41C operated in order to input a measurement stop instruction, a memory switch 41D operated in order to input an instruction for causing information such as blood pressure data to be read out from the memory 43 and displayed on the display unit 40, and a timer set switch 41E operated in order to input an instruction for setting the timer 45. The operation unit 41 can also include an inspection switch 41F discussed later.

The main body portion 10 further includes a pump 51, an exhaust valve (hereinafter, valve) 52 and a tank 57 that serve as a mechanism for adjusting the internal pressure (cuff pressure) of the air bladder 21 contained in the cuff 20. The pump 51 and the valve 52 function mainly as a mechanism for adjusting the cuff pressure when measuring blood pressure, and the tank 57 has a fixed capacity and functions mainly as a pressure adjustment mechanism for detecting abnormality of a pressure sensor 32. The main body portion 10 is further provided with a switching valve 56 for selectively connecting one of the two adjustment mechanisms to the cuff 20 (air bladder 21) via an air tube 31, and a switching valve drive circuit 55 for controlling the open/close operation of the switching valve 56. The main body portion 10 is provided, in association with the tank 57, with a temperature sensor 571 serving as a temperature detector. The temperature sensor 571 detects the ambient temperature of the tank 57, and outputs the detected temperature to the CPU 100. The CPU 100, based on the input signal from the temperature sensor 571, calculates a temperature coefficient that is based on the degree of expansion of air in the tank 57. The CPU 100 calculates this temperature coefficient using a prescribed arithmetic equation. Alternatively, the CPU 100 decides to search a table stored in the memory 42 in which temperatures are associated with temperature coefficients.

The switching valve 56 has connected thereto an air tube 31 (hereinafter, first air tube 31) to which the pressure sensor 32, the pump 51 and the valve 52 are commonly connected, an air tube 31 (hereinafter, second air tube 31) connected to the cuff 20 (air bladder 21) and an air tube 31 (hereinafter, third air tube 31) connected to the tank 57. The switching valve 56 selectively connects one of the second air tube 31 and the third air tube 31 to the first air tube 31, in accordance with a switching signal 58 provided by the switching valve drive circuit 55. Here, "the switching valve 56 is switched to the cuff 20 side" refers to connecting the second air tube 31 to the first air tube 31, and "the switching valve 56 is switched to the tank 57 side" refers to connecting the third air tube 31 to the first air tube 31.

The main body portion 10 further has an oscillation circuit 33 connected to the pressure sensor 32, a pump drive circuit 53 connected to the pump 51, and a valve drive circuit 54 connected to the valve 52. The output signal of the oscillation circuit 33 is provided to the CPU 100.

The pump 51 supplies air to the air bladder 21 in order to increase the cuff pressure, and supplies air to the tank 57 in order to detect abnormality of the pressure sensor 32. The valve 52 is opened and closed in order to discharge or enclose air in the air bladder 21 or the tank 57. The pump drive circuit 53 controls the drive of the pump 51 based on a control signal provided by the CPU 100. The pump 51 sends air at a fixed flow rate per unit time, in accordance with the voltage level applied by the pump drive circuit 53. The valve drive circuit 54 opens and closes the valve 52 based on a control signal provided by the CPU 100. The switching valve drive circuit 55 generates the switching signal 58 based on a control signal provided by the CPU 100, and outputs the generated switching signal 58 to the switching valve 56.

The pressure sensor 32 is a capacitance pressure sensor whose capacitance value changes according to the detected cuff pressure. The oscillation circuit 33 is connected to the pressure sensor 32, and oscillates based on the capacitance value of the pressure sensor 32. The oscillation circuit 33 thereby outputs a signal (hereinafter, frequency signal) having a frequency that depends on the capacitance value of the pressure sensor 32 to the CPU 100. The CPU 100 detects pressure by converting the frequency signal input from the oscillation circuit 33 into pressure.

Figure 3:
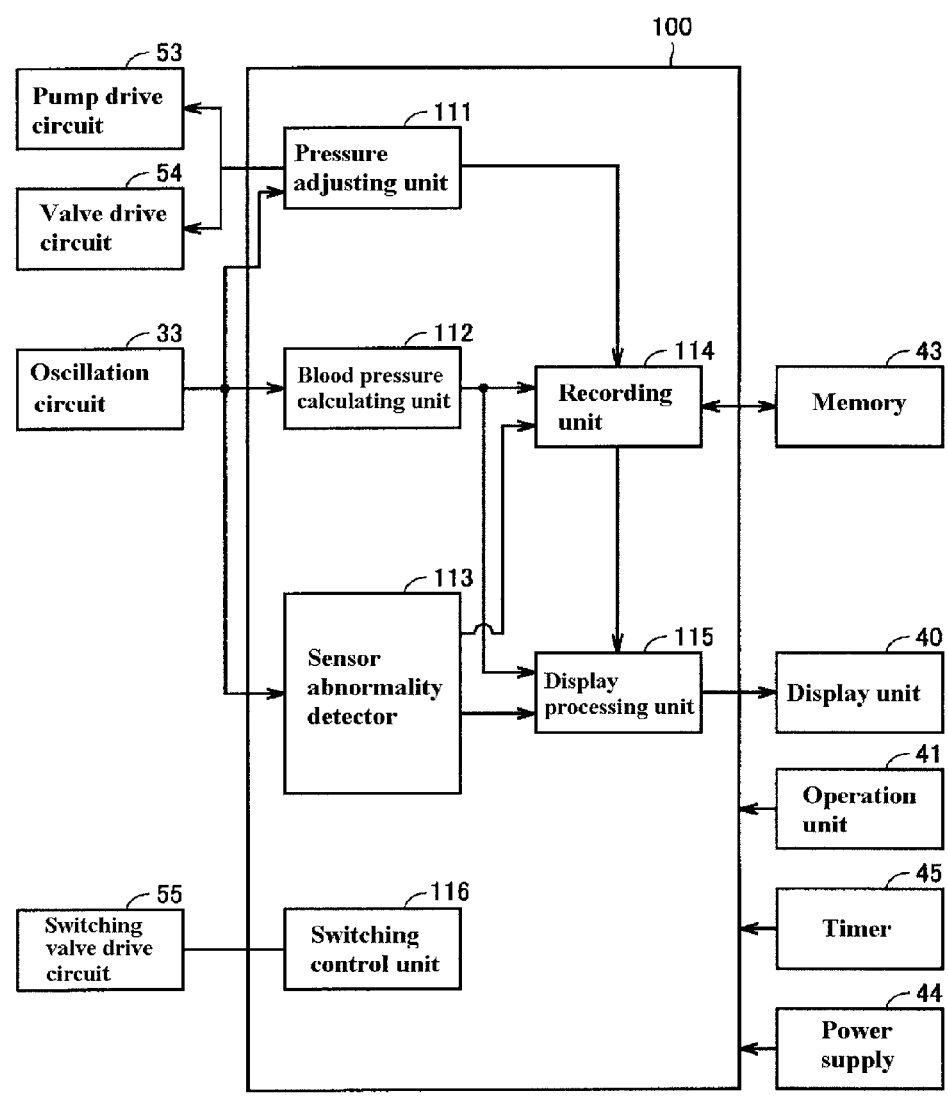
FIG. 3 is a functional configuration diagram of the electronic sphygmomanometer according to one or more embodiments of the present invention.

FIG. 3 shows the functional configuration of the electronic sphygmomanometer 1. In FIG. 3, only the portion of peripheral circuitry of the CPU 100 that directly perform input/output with the CPU 100 is shown.

Referring to FIG. 3, the CPU 100 is provided with a pressure adjusting unit 111, a blood pressure calculating unit 112, a sensor abnormality detector 113, a recording unit 114, a display processing unit 115, and a switching control unit 116. The switching control unit 116 controls the switching valve drive circuit 55.

The pressure adjusting unit 111 adjusts the cuff pressure by controlling the pump 51 and the valve 52 via the pump drive circuit 53 and the valve drive circuit 54, and causing air to flow into or be discharged from the air bladder 21 via the air tubes 31. Here, the configuration including the pressure sensor 32, the pump 51 and the valve 52 is called an air system.

The blood pressure calculating unit 112 detects pulse wave amplitude information based on the frequency signal (this frequency signal indicates a pressure information signal) input from the oscillation circuit 33, and calculates systolic blood pressure and diastolic blood pressure in accordance with the oscillometric method based on the detected pulse wave amplitude information, as well as calculating the pulse rate per prescribed time period based on the detected pulse wave amplitude information. Specifically, in the process of gradually increasing (or decreasing) the cuff pressure to a prescribed value by the pressure adjusting unit 111, pulse wave amplitude information is detected based on the output from the oscillation circuit 33, and systolic blood pressure and diastolic blood pressure of the person being measured are calculated based on the detected pulse wave amplitude information. A conventionally known method can be applied to the blood pressure calculation and the pulse calculation performed by the blood pressure calculating unit 112 in accordance with the oscillometric method.

The sensor abnormality detector 113 detects abnormality of the pressure sensor 32 by inputting the frequency signal output from the oscillation circuit 33 and analyzing the input signal.

The recording unit 114 reads out data from the memory 43 or writes data to the memory 43. Specifically, data (blood pressure measurement data) output from the blood pressure calculating unit 112 is input, and the input data is stored in a prescribed storage area of the memory 43. Further, data (result of abnormality detection of the pressure sensor 32) output from the sensor abnormality detector 113 is input, and the input data is stored in a prescribed storage area of the memory 43. Also, the recording unit 114 reads out measurement data from a prescribed storage area of the memory 43 based on operation of the memory switch 41D of the operation unit 41, and outputs the read data to the display processing unit 115.

The display processing unit 115 inputs data provided thereto, converts the input data to a displayable form, and displays the resultant data on the display unit 40.

Figure 4:
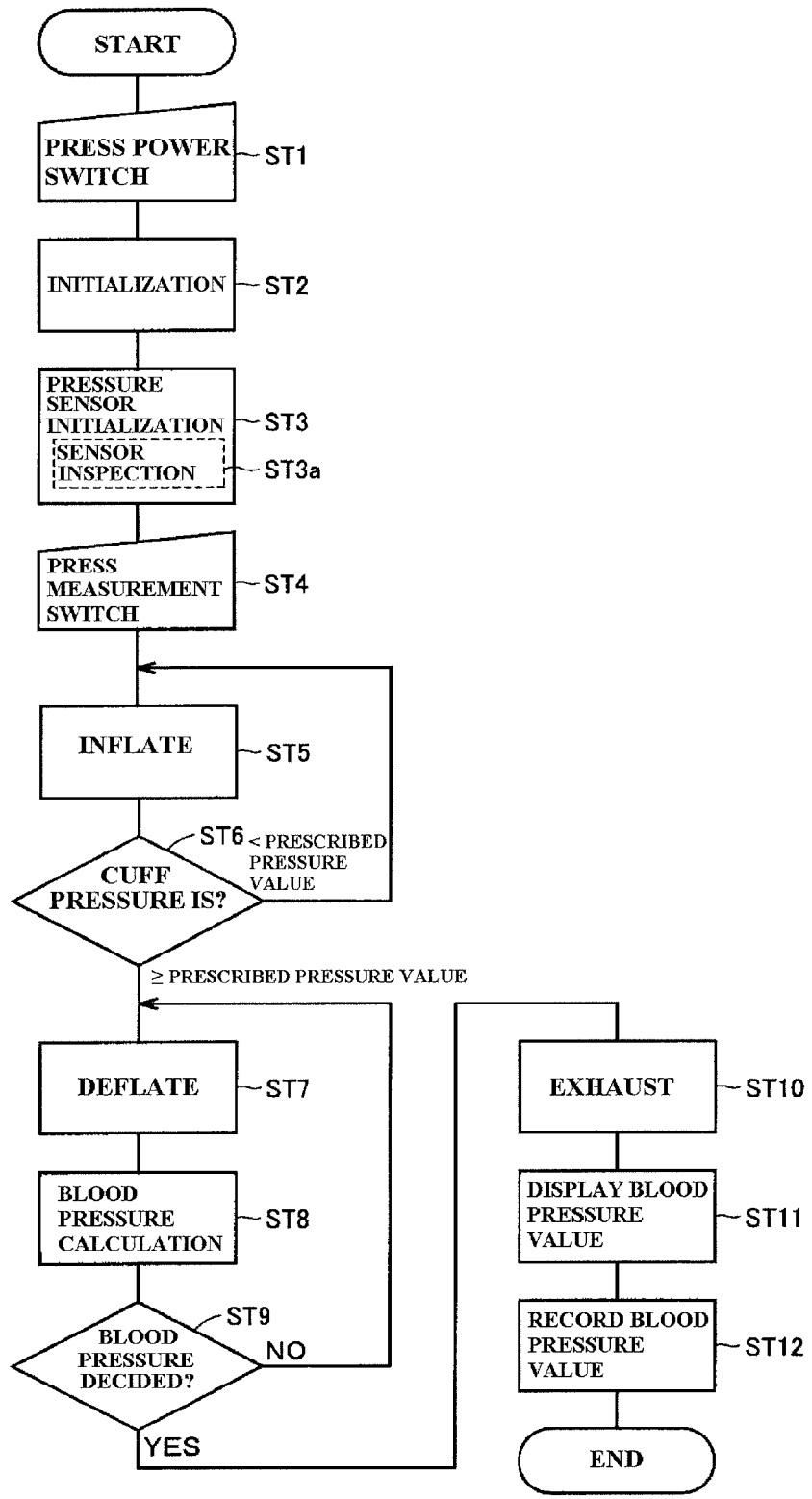
FIG. 4 is a flowchart of blood pressure measurement processing according to one or more embodiments of the present invention.

The processing procedure of blood pressure measurement according to the present embodiment is described, with reference to FIG. 4. A flowchart showing the processing procedure in FIG. 4 is stored as a program in the memory 42 in advance, and the blood pressure measurement processing of FIG. 4 is realized by the CPU 100 reading out the program from the memory 42 and executing commands.

First, when the person being measured operates (presses) the power switch 41A (step ST1), the CPU 100 initializes an unshown work memory (ST2).

Subsequently, a 0 mm Hg adjustment of the pressure sensor 32 is performed (ST3). The details of the 0 mm Hg adjustment are discussed later. Abnormality of the pressure sensor 32 is detected at the time of the 0 mm Hg adjustment (step ST3a). The details of this abnormal detection are discussed later.

Here, the person being measured puts on the cuff 20 by wrapping the cuff around the measurement site as shown in FIG. 1. When the person being measured operates (presses) the measurement switch 41B after wrapping around the cuff 20 (step ST4), the pressure adjusting unit 111 outputs a control signal to the pump drive circuit 53 and the valve drive circuit 54. The pump drive circuit 53 and the valve drive circuit 54 drive the pump 51, after closing off the valve 52 based on the control signal. The cuff pressure is thereby gradually increased to a prescribed pressure (steps ST5, ST6). The pressure adjusting unit 111 detects the cuff pressure based on the frequency signal input from the oscillation circuit 33, and compares the detected cuff pressure with the prescribed pressure indicated by the data read out from the memory 42. Inflation is continued until it is determined that the detected cuff pressure indicates the prescribed pressure, based on the comparison result. That is, inflation (step ST5) is continued for the duration that the condition "cuff pressure<prescribed inflation value" is determined to be satisfied at step ST6.

After it is determined, based on a comparison result, that the cuff pressure has reached the prescribed pressure (condition that "cuff pressure≥prescribed inflation value" is satisfied at step ST6), the pressure adjusting unit 111 outputs a control signal to the pump drive circuit 53 and the valve drive circuit 54. The pump drive circuit 53 and the valve drive circuit 54 stop the inflation by stopping the pump 51 based on the control signal. Thereafter, control is performed so as to gradually open the valve 52. The process thereby shifts from inflation to deflation, and the cuff pressure gradually decreases (step ST7).

In this deflation process, the blood pressure calculating unit 112 detects pulse wave amplitude information based on the frequency signal output from the oscillation circuit 33, that is, based on the cuff pressure signal detected by the pressure sensor 32, and performs a prescribed arithmetic operation on the detected pulse wave amplitude information. Systolic blood pressure and diastolic blood pressure are calculated by this arithmetic operation (step ST8, ST9). Pulse wave amplitude information represents an arterial volume change component of the measurement site, and is included in the detected cuff pressure signal. Note that blood pressure measurement is not limited to the deflation process, and may be performed in the inflation process (step ST5).

Once the measured blood pressure is decided as a result of the systolic blood pressure and the diastolic blood pressure being calculated (YES at step ST9), the pressure adjusting unit 111 fully opens the valve 52 via the valve drive circuit 54, and quickly exhausts the air in the cuff 20 (step ST10).

Data indicating the blood pressure calculated by the blood pressure calculating unit 112 is output to the display processing unit 115 and the recording unit 114. The display processing unit 115 inputs the blood pressure data, and displays the input blood pressure data on the display unit 40 (step ST11). The recording unit 114 inputs the blood pressure data, and stores the input blood pressure data in a prescribed storage area of the memory 43, in association with time data input from the timer 45 (step ST12).

Note that the blood pressure calculating unit 112 can also calculate a pulse rate based on the detected pulse wave amplitude information. The calculated pulse rate is displayed on the display unit 40 by the display processing unit 115, and stored in the memory 43 by the recording unit 114 in association with the blood pressure data.

In the display and storage of such data, the results of abnormality detection of the pressure sensor 32 detected at step ST3a are also displayed, as well as being stored in memory.

Data indicating the measurement date/time, the blood pressure value (systolic blood pressure SYS, diastolic blood pressure DIA), the pulse rate, and the result of abnormality detection of the pressure sensor 32 are stored in association with each other in the memory 43 whenever blood pressure measurement is performed.

Also, exemplary storage contents of the memory 43 in the case where the abnormality inspection of the pressure sensor 32 is performed at a prescribed time interval or by a prescribed user operation rather than every blood pressure measurement are shown in FIG. 5. Referring to (A) and (B) of FIG. 5, measurement data is stored per record. Each record includes ID (Identifier) data D1 identifying the record, identification data D2 of the person being measured, measurement date/time data D3, blood pressure value and pulse rate data D4, and result data D5 of the abnormality detection of the pressure sensor 32.

As shown in the diagram, in the case where it is judged, as a result of the current abnormality inspection, that the pressure sensor 32 is abnormal, a flag ("NG") indicating that the pressure sensor 32 is possibly abnormal is added, as data D5, to the records of the blood pressure measurement results stored during the period from the previous inspection day to the current inspection day. Because the possibility that the pressure sensor 32 was abnormal at the time of measurement can thereby be presented for each piece of blood pressure measurement data in the case where measurement data is read out from the memory 43 and displayed on the display unit 40, an index of the reliability of the data can be shown regarding the blood pressure values presented to the user at the same time.

Accordingly, the user (person being measured) can judge whether the pressure sensor 32, which is the most important element for calculating blood pressure, is normal or abnormal. Hence, even in the case where a measured blood pressure value differs greatly from the normal value (e.g., value measured the previous day, value measured at a hospital, etc.), it is possible to avoid a situation where the person being measured is made to feel anxious because of not knowing whether the difference is due physiological information relating to the living body or to a malfunction of the pressure sensor 32.

Here, the concept of the blood pressure calculation method using the oscillometric method in the present embodiment is described. In (A) of FIG. 6, gradually decreasing cuff pressure is shown on the time axis clocked by the timer 45. In (B) of FIG. 6, an envelope curve 600 of pulse wave amplitude corresponding to abovementioned pulse wave amplitude information is shown on an identical time-axis. The envelope curve 600 of pulse wave amplitude is detected by extracting, in time series, the pulse wave amplitude signal superimposed on the signal (cuff pressure) from the pressure sensor 32.

Figure 6:
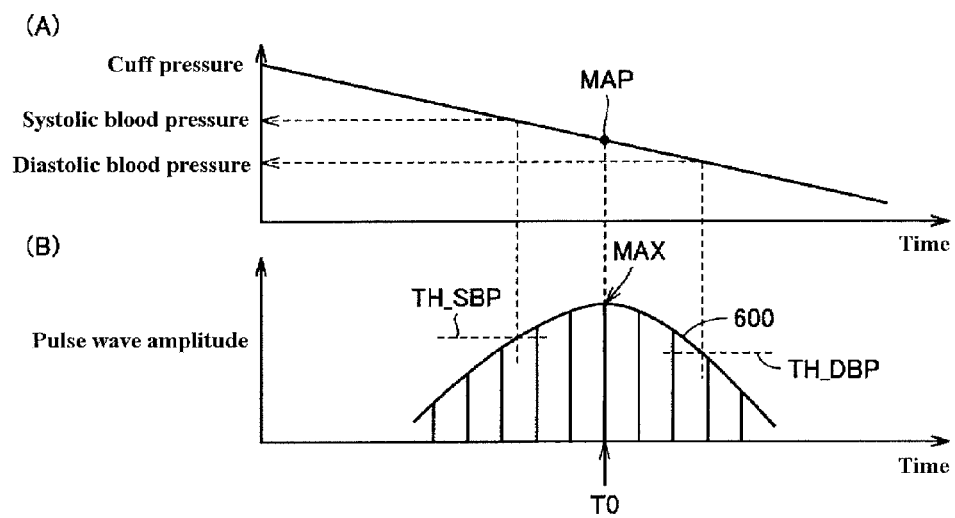
FIG. 6 is a diagram illustrating a blood pressure calculation procedure according to one or more embodiments of the present invention.

Referring to (A) and (B) of FIG. 6, the blood pressure calculating unit 112, on detecting the maximum amplitude value MAX on the envelope curve of pulse wave amplitude, calculates two thresholds TH_DBP and TH_SBP by multiplying the maximum value by prescribed constants (e.g., 0.7 and 0.5). The cuff pressure at the point where the threshold TH_DBP intersects the envelope curve 600 on the side on which the cuff pressure is lower than a cuff pressure MAP (average blood pressure) at the point in time T0 at which the maximum value MAX is detected is then calculated as the diastolic blood pressure. Also, the cuff pressure at the point where the threshold TH_SBP intersects the envelope curve 600 on the side on which the cuff pressure is higher than the cuff pressure MAP is calculated as the systolic blood pressure.

Acquisition of Condition Data for Pressure Sensor Abnormality Detection

In the present embodiment, prescribed condition data for abnormality detection of the pressure sensor 32 is acquired in advance such as at the time of factory shipment of the electronic sphygmomanometer 1, and the acquired prescribed condition data is stored in the memory 42. The procedure for acquiring this prescribed condition data is described.

Figure 7:
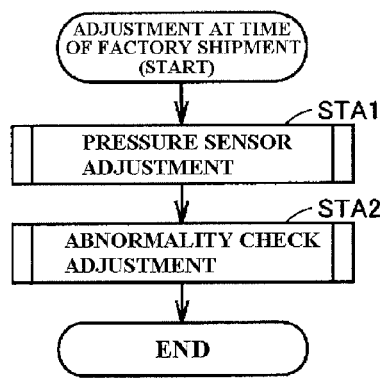
FIG. 7 is a flowchart schematically showing an adjustment procedure at the time of factory shipment of the electronic sphygmomanometer according to one or more embodiments of the present invention.

A flowchart of schematic processing for prescribed condition acquisition at the time of factory shipment is shown in FIG. 7. First, processing for adjusting the pressure sensor 32 is performed (step STA1). Prescribed condition data for 0 mm Hg correction is detected by the adjustment processing. Subsequently, prescribed condition data for abnormality detection of the pressure sensor 32 is detected (step STA2).

Figure 8:
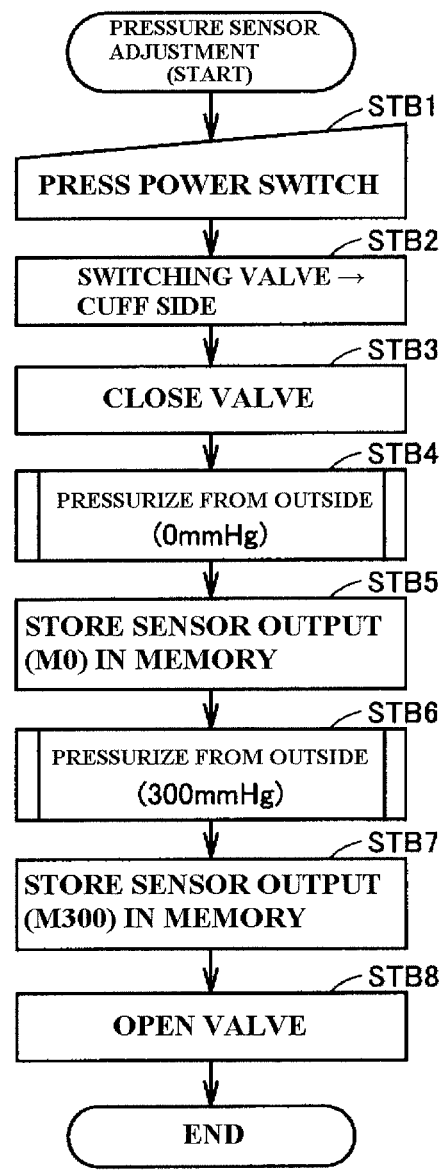
FIG. 8 is a flowchart of pressure sensor adjustment in FIG. 7.

The pressure sensor adjustment processing (step STA1) shown in FIG. 7 is described, with reference to FIG. 8. Note that a pressurization device is connected to the electronic sphygmomanometer 1 instead of the cuff 20.

First, an operator operates the power switch 41A (step STB1). Subsequently, the switching control unit 116 controls the switching valve drive circuit 55. The switching valve drive circuit 55 outputs the switching signal 58 in response to the control, and switches the switching valve 56 to the cuff 20 side (step STB2). Air thereby flows, via the air tubes 31, between the air system and the pressurization device which is connected instead of the cuff 20.

Subsequently, the pressure adjusting unit 111 controls the valve drive circuit 54 so as to close off the valve 52. The valve 52 is closed off in response to this control (step STB3).

The output of the pressure sensor 32 when prescribed pressure values (0 mm Hg, 300 mm Hg) are applied by the connected pressurization device (in the present embodiment, this refers to frequencies M0 and M300 of the output signal of the oscillation circuit 33) is measured, and the measured values are stored in a prescribed storage area of the memory 43 (steps STB4 to STB7). The prescribed pressure values (0 mm Hg, 300 mm Hg) are dependent on the electronic sphygmomanometer 1 being designed to be able to measure blood pressures from 0-299 mm Hg. These measured values are not rewritable in the memory 43, and will not be erased. The prescribed condition data for 0 mm Hg correction at the time of blood pressure measurement is thereby acquired. A linear equation of characteristics L1 in FIG. 10 discussed later can thereby be detected.

Thereafter, the valve drive circuit 54 opens the valve 52, and the air enclosed in the air system is quickly exhausted (step STB8).

Next, the prescribed condition data detection processing (step STA2 of FIG. 7) for abnormality detection of the pressure sensor 32 is described with reference to FIG. 9.

Figure 9:
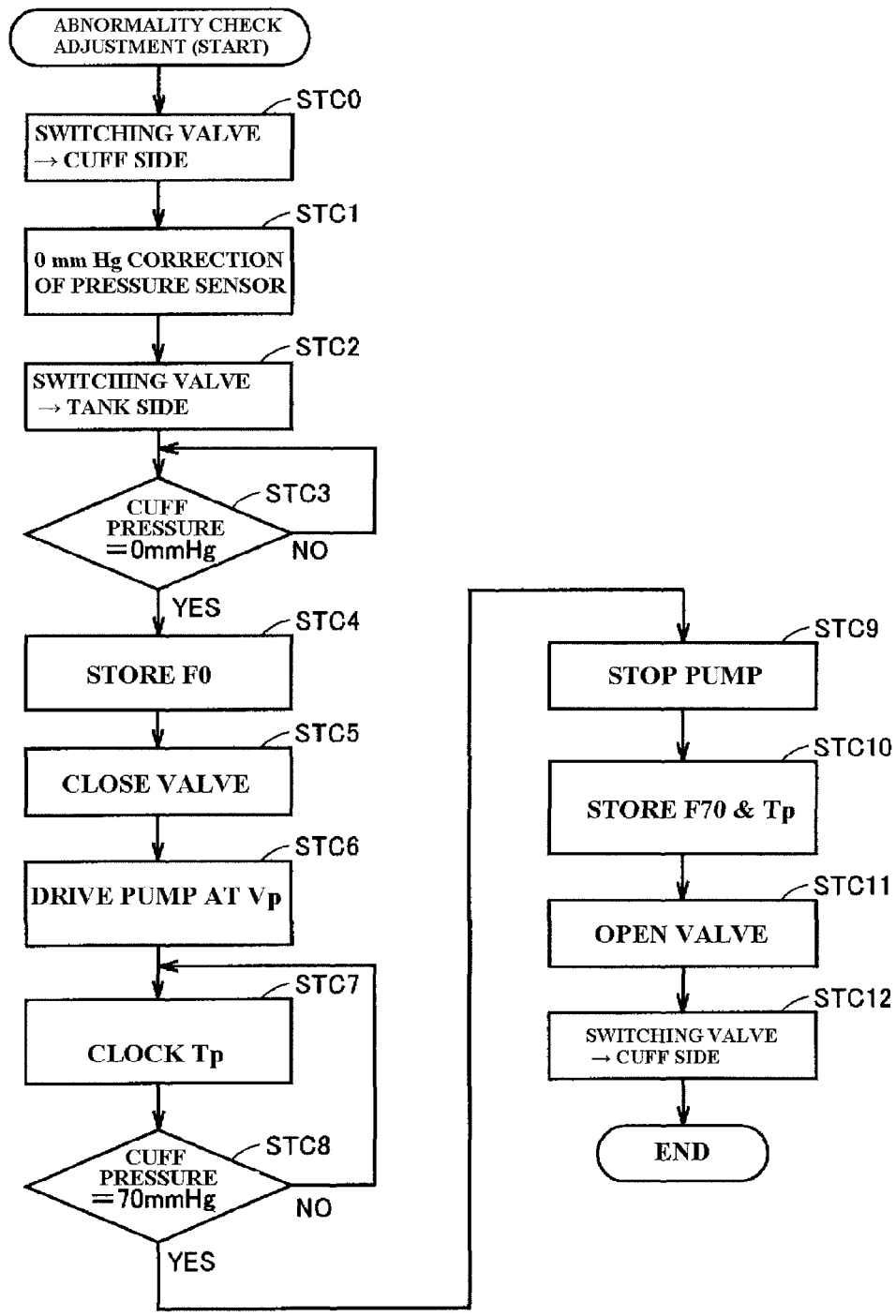
FIG. 9 is a flowchart of adjustment for pressure sensor abnormality detection in FIG. 7.

Referring to FIG. 9, first the switching control unit 116 controls the switching valve drive circuit 55. As a result of this control, the switching valve drive circuit 55 switches the switching valve 56 to the cuff 20 side (step STC0). At this time, the valve 52 is open, and stays in an open state until step STC5 discussed later.

Subsequently, 0 mm Hg correction processing on the pressure sensor 32 is performed (step STC1).

Thereafter, the switching control unit 116 controls the switching valve drive circuit 55. The switching valve drive circuit 55, in response to the control, outputs the switching signal 58, and switches the switching valve 56 from the cuff 20 side to the tank 57 side (step STC2). Subsequently, the sensor abnormality detector 113 detects whether the cuff pressure, that is, the internal pressure of the tank 57, indicates 0 mm Hg, based on the output signal of the oscillation circuit 33 (step ST3). When it is detected that the cuff pressure indicates 0 mm Hg (YES at step STC3), the CPU 100 stores the frequency signal output by the oscillation circuit 33 in the memory 43 as a sensor output F0 (step STC4). Next, the pressure adjusting unit 111 controls the valve drive circuit 54. In response to this control, the valve drive circuit 54 closes the open valve 52 (step STC5).

Subsequently, the pressure adjusting unit 111 controls the pump drive circuit 53. The pump drive circuit 53, in response to the control, supplies an arbitrary fixed voltage Vp to the pump 51, and operates the pump 51. Because the number of rotations of the pump 51 is decided by the supplied voltage, the pump rotates for a number of times that depends on the fixed voltage Vp, and supplies air to the tank 57 (step STC6).

Subsequently, the pressure adjusting unit 111 clocks the elapsed time from the drive start of the pump 51 as a drive time period Tp using the timer 45 (step STC7). The pump is continually driven and time is continually clocked until it is detected that the frequency signal output by the oscillation circuit 33 indicates a prescribed pressure (e.g., internal pressure of the tank 57 is 70 mm Hg) (YES at step STC8).

When it is determined that the internal pressure of the tank 57 indicates 70 mm Hg (YES at step STC8), the pressure adjusting unit 111 controls the pump drive circuit 53. In response to this control, the pump drive circuit 53 stops voltage supply to the pump 51, and causes rotation of the pump 51 to stop (step STC9). Supply of air to the tank 57 is thereby stopped.

Thereafter, data indicating an output F70 (frequency signal output by the oscillation circuit 33) of the pressure sensor 32, the drive time period Tp of the pump 51, and the fixed voltage Vp are stored in the memory 43 via the recording unit 114 (step STC10).

Thereafter, the pressure adjusting unit 111 controls the valve drive circuit 54. In response to the control, the valve drive circuit 54 opens the closed valve 52 (step STC11). The air in the tank 57 is thereby quickly exhausted.

Thereafter, the switching control unit 116 controls the switching valve drive circuit 55. The switching valve drive circuit 55 thereby switches the switching valve 56 from the tank 57 side to the cuff 20 side (step STC12). An air channel between the air system and the cuff 20 is thereby established.

0 mm Hg Correction of Pressure Sensor

The blood pressure calculating unit 112, when measuring blood pressure, compares the measured values of the calibrated output of the pressure sensor acquired at the time of manufacture (frequency signal data M0 and M300) with the measured value of the output of the pressure sensor at the time of initialization, and performs 0 mm Hg correction of the pressure sensor 32 at the current point in time based on the comparison result.

Specifically, the blood pressure calculating unit 112 calculates a pressure value P (mm Hg) in accordance with Equation 1, where "M0" and "M300" represent the measured values of the output of the pressure sensor 32 when calibrated for 0 mm Hg and 300 mm Hg at the time of manufacture, "U0" represents the measured value of the output at the time of initialization of the pressure sensor 32 at step ST3, and "f" represents the frequency of the signal currently output from the oscillation circuit 33. The calculated pressure value P is equivalent to the cuff pressure in (A) of FIG. 6.

$$\text{Pressure value } P=\{(f-U0)/(M300-M0)\}\times 300 \quad \text{(Eq. 1)}$$

Figure 10:
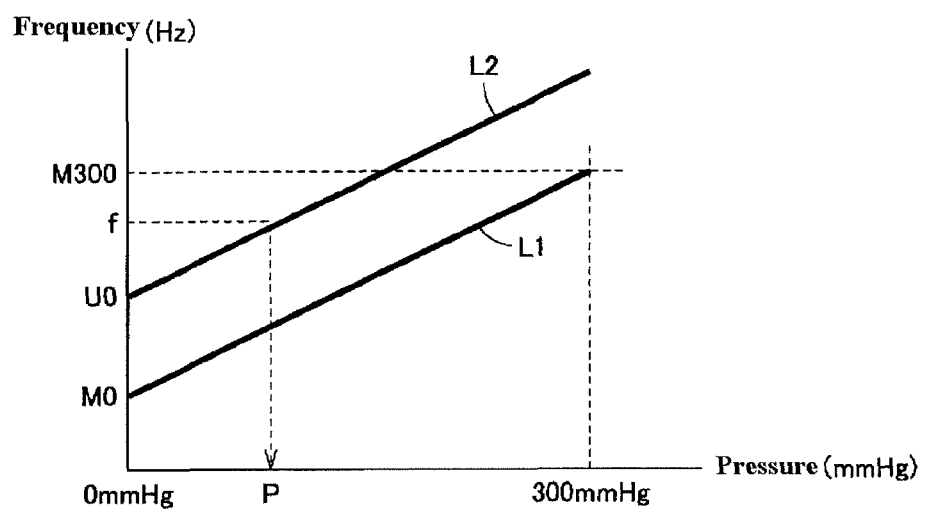
FIG. 10 is a diagram illustrating the characteristics of a pressure sensor.

Calculation of the pressure value P in accordance with the above-mentioned Equation 1 is further described, with reference to the graph of FIG. 10 showing the characteristics of the pressure sensor 32. In the graph of FIG. 10, pressure (mm Hg) indicating cuff pressure is shown on the horizontal axis, and frequency (Hz) of the output signal of the oscillation circuit 33 is shown on the vertical axis. The characteristics L1 of the pressure sensor 32 at the time of manufacture of the electronic sphygmomanometer 1 and the current characteristics L2 of the pressure sensor 32 are shown in FIG. 10.

If the characteristics L1 of the pressure sensor 32 at the time of manufacture and the current characteristics L2 of the pressure sensor are the same, pressure value $P=(f-M0)/(M300-M0)\times 300$ (Eq. 2) is satisfied, but in reality the characteristics of the pressure sensor 32 cannot maintain the characteristics L1 at the time of manufacture due to various factors such as usage, and the characteristics L1 change to the current characteristics L2, for example. The output U0 at the time of initialization of the pressure sensor 32 arises with this change in characteristics. Accordingly, using the output U0 at the time of initialization of the pressure sensor 32 enables Equation 2 to be rewritten as Equation 1.

The procedure by which the output U0 is thus detected to derive Equation 1 is called 0 mm Hg correction.

Pressure Sensor Initialization at the Time of Blood Pressure Measurement

Figure 11:
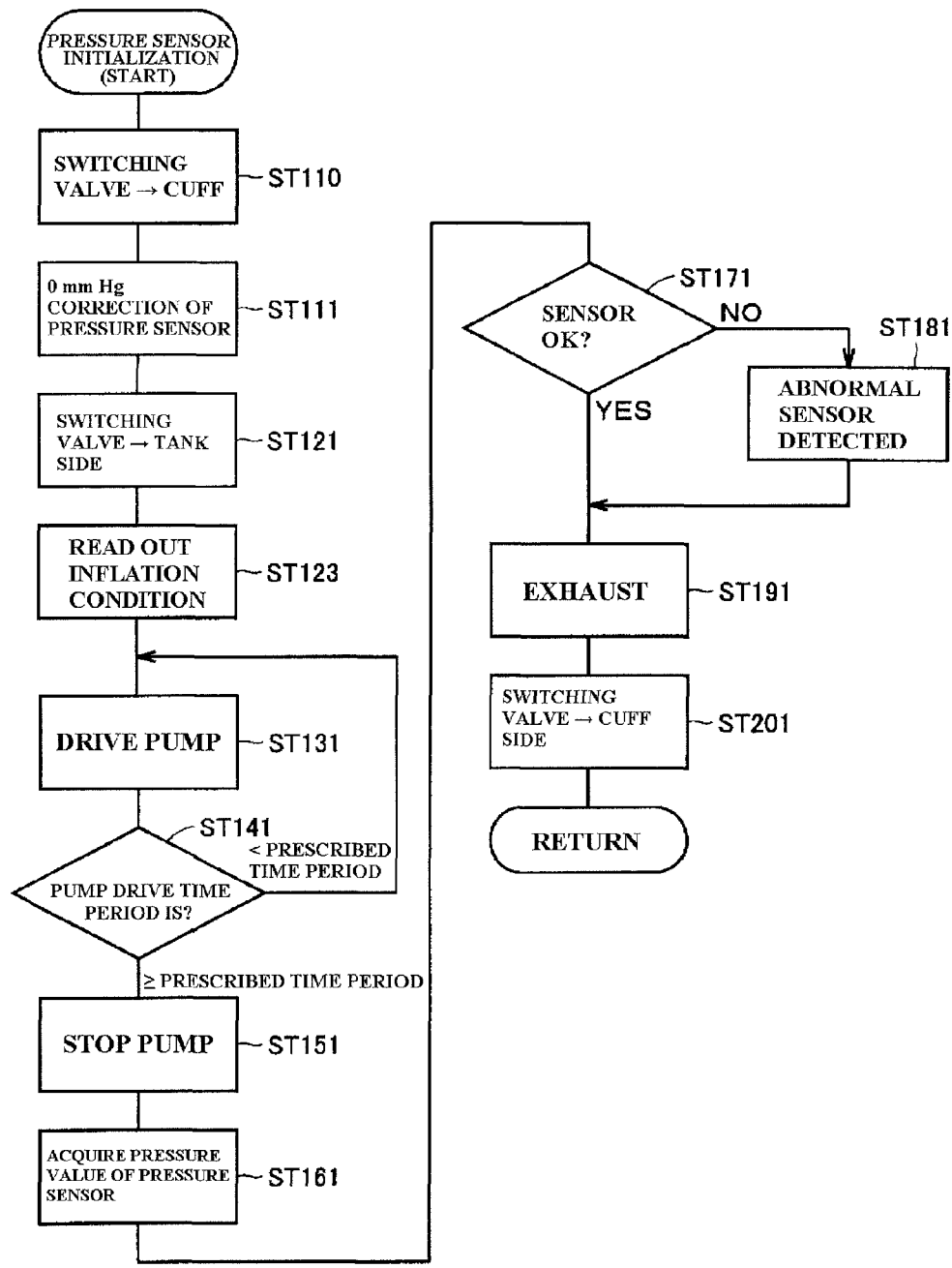
FIG. 11 is a flowchart of pressure sensor abnormality detection processing according to one or more embodiments of the present invention.

The procedure for initializing the pressure sensor 3 (step ST3) which includes abnormality detection of the pressure sensor 32 (step ST3a) is described, with reference to the flowchart of FIG. 11. Processing in accordance with this flowchart is carried out in the aforementioned step ST3. Note that it is assumed that air in the tank 57 has been sufficiently exhausted and the internal pressure is 0 mm Hg.

In this processing, the output value of the pressure sensor 32 when a prescribed amount of air has been sent to the tank 57 is compared with the values of prescribed condition data detected in advance, and abnormality of the pressure sensor 32 is detected, based on the comparison result.

At the time of initialization of the pressure sensor 32, the switching control unit 116 first outputs a control signal to the switching valve drive circuit 55. The switching valve drive circuit 55 outputs the switching signal 58 based on the control signal. The switching valve 56 is switched from the tank 57 side to the cuff 20 side in accordance with the switching signal 58 (step ST110). Accordingly, the first air tube 31 and the second air tube 31 are connected via the switching valve 56, and an air channel is constituted by both tubes. 0 mm Hg correction of the pressure sensor 32 is performed in this state (step ST111). In other words, data f0 (equivalent to data U0 in FIG. 10) of the frequency signal of the oscillation circuit 33 when the air in the air bladder 21 of the cuff 20 has been sufficiently exhausted to achieve a zero cuff pressure is detected and temporarily stored in the memory 43.

Thereafter, the switching control unit 116 outputs a control signal to the switching valve drive circuit 55. The switching valve drive circuit 55 switches the switching valve 56 to the tank 57 side, based on the control signal. Accordingly, the air tube connected to the first air tube 31 via the switching valve 56 is switched from the second air tube 31 to the third air tube 31. Air flows in the direction of the tank 57 side as a result of the switching valve 56 (step ST121).

Next, the CPU 100 reads out prescribed condition data (voltage Vp, time period Tp) from the memory 43 (step ST123). The valve 52 is then closed off by the valve drive circuit 54, and the prescribed voltage Vp is applied to the pump 51 for the read fixed time period Tp by the pump drive circuit 53. The pump 51 thereby rotates and air is sent to the tank 57 (steps ST131 to ST151). The pressure sensor abnormality detector 113 detects the output value of the pressure sensor 32 (data f70 of the frequency signal of the oscillation circuit 33) when the fixed time period Tp has elapsed (step ST161), and temporarily stores the detected data f70 in the memory 43.

The CPU 100 then reads out data f0 and data F0 from the memory 43, and calculates a difference MD of both pieces of read data. The difference MD serves as the aforementioned 0 mm Hg correction amount. Also, data f70 and data F70 are read out from the memory 43, and a difference Δf70 of both pieces of read data is calculated. A difference Δf of the difference Δf70 and the difference MD is then compared with a prescribed value (e.g., frequency value equivalent to 3 mm Hg), and abnormality of the pressure sensor 32 is detected based on the comparison result (step ST171).

Specifically, when it is detected, based on the comparison result, that the difference Δf is less than or equal to a prescribed value, it is judged that the pressure sensor 32 is normal (YES at step ST171), whereas when it is detected that the difference Δf is greater than the prescribed value (NO at step ST171), it is judged that the pressure sensor 32 is abnormal (step ST181). In the case where abnormality of the pressure sensor 32 is detected, this information is displayed on the display unit 40.

Once abnormality detection of the pressure sensor 32 has ended, the valve 52 is opened by the valve drive circuit 54, and all the air in the tank 57 is exhausted (ST191). Thereafter, the switching control unit 116 outputs a control signal to the switching valve drive circuit 55. The switching valve drive circuit 55 switches the switching valve 56 to the cuff 20 side, based on the control signal. Accordingly, the air tube connected to the first air tube 31 via the switching valve 56 is switched from the third air tube 31 to the second air tube 31. Air thereby flows in the direction of the cuff 20 side (step ST201). Initialization of the pressure sensor 32 (step ST3) is thereby ended.

Because the required volume (capacity) of the tank 57 need only be the capacity required for the inspection (i.e., amount of air supplied to the tank 57 in the time period Tp during which the pump 51 has the voltage Vp applied thereto and rotates), being a comparatively small volume such as 70 mm Hg, for example, device miniaturization is not inhibited even when the tank 57 is used in order to detect abnormality of the pressure sensor 32.

Note that although the internal pressure of the tank 57 is fixed at 70 mm Hg, and the supply flow rate to the tank 57 by the pump 51 is fixed by the product of the applied voltage Vp and the time period Tp, these values may be changed according to the environmental conditions around the electronic sphygmomanometer 1, or more specifically, around the tank 57.

For example, the fluid densities in the tank 57 differ even at the same pressure when the ambient temperatures at the time of manufacture and at the time of blood pressure measurement differ, making it necessary to change the amount of air allowed to flow into the tank 57 by adjusting the drive time period and/or drive voltage of the pump 51 depending on the temperature. In other words, the drive time period and/or drive voltage of the pump 51 may be changed by summing the temperature coefficients that are based on the degree of expansion of air which is dependent on the temperature detected by the temperature sensor 571.

Exemplary Display

Figure 12:
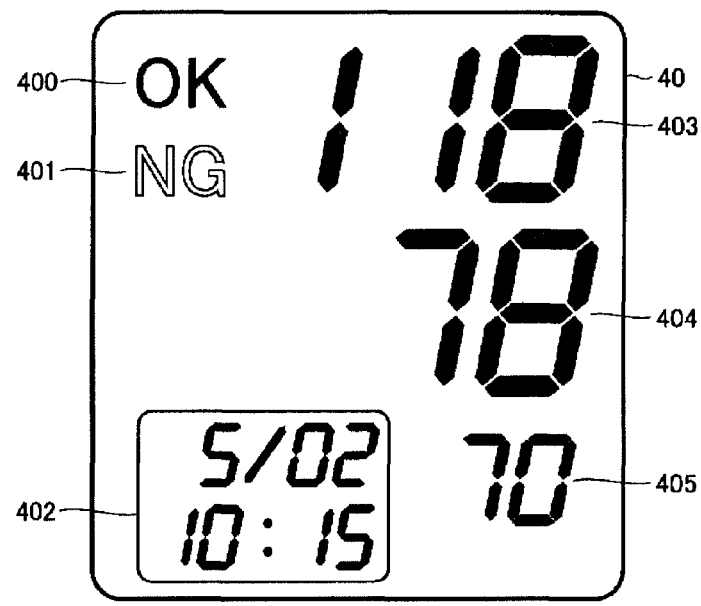
FIG. 12 is a diagram showing an example of display according to one or more embodiments of the present invention.

FIG. 12 shows exemplary display of a result of abnormality detection of the pressure sensor 32 on the display unit 40. In FIG. 12, the display processing unit 115 turns off the characters "NG" and only turns on the characters "OK" if the pressure sensor 32 is normal. If abnormal, the characters "OK" are turned off and the characters "NG" are turned on. On this display, measurement time data 402 clocked by the timer 45 and systolic blood pressure data 403, diastolic blood pressure data 404 and pulse rate data 405 that result from the blood pressure measurement are displayed together with the "NG"/"OK" display.

The recorded data D3 to D5 are also read out and displayed on the display of FIG. 12, in the case where the memory switch 41D of the operation unit 41 is operated and measurement data in the memory 43 is read out and displayed.

The person being measured is able to obtain the timing at which the manufacturer will be requested to calibrate the pressure sensor 32, by checking such a display. Accordingly, performing blood pressure measurement without realizing that the pressure sensor 32 is abnormal can be avoided, and the reliability of measured blood pressure values can be improved.

Manual Switching of Air Tubes 31

Figure 13:
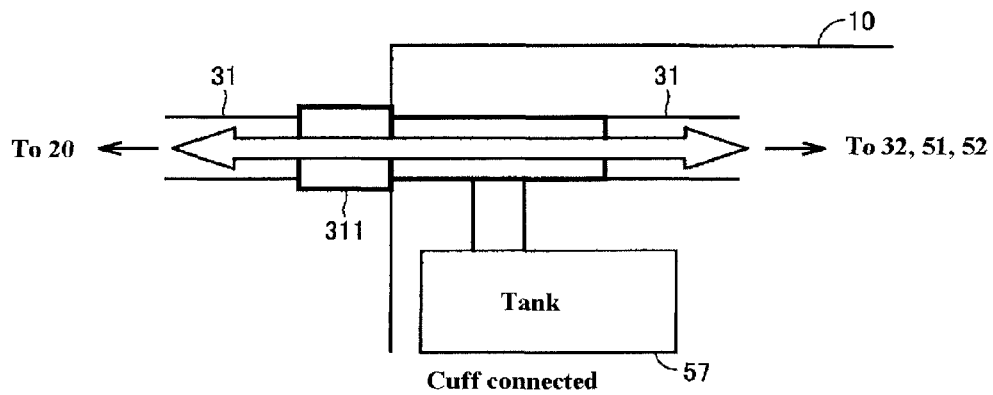
FIG. 13 is a diagram showing the connection mode of air tubes in the case of using a measurement plug according to one or more embodiments of the present invention.
Figure 14:
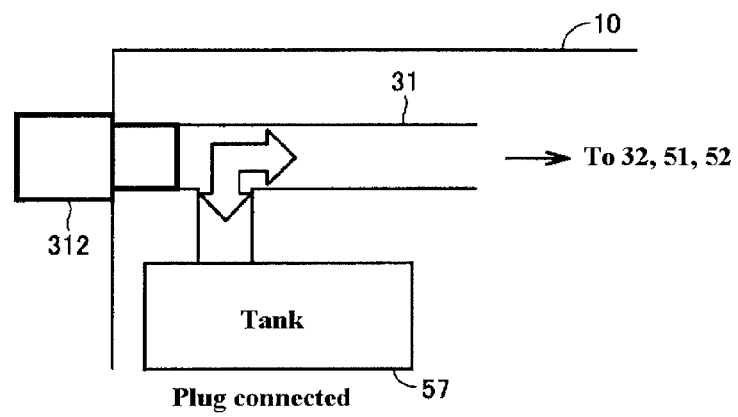
FIG. 14 is a diagram showing the connection mode of air tubes in the case of using an inspection plug according to one or more embodiments of the present invention.

As described above, switching is performed automatically so as to connect one of the third air tube 31 on the tank 57 side and the second air tube 31 on the cuff 20 side to the first air tube 31 using the switching valve 56, but switching may be performed manually as shown in FIG. 13 and FIG. 14. In FIG. 13 and FIG. 14, the thick arrow indicates the direction in which air flows.

In order to perform manual switching, an inspection plug 312 and a measurement plug 311 that are detachable from the main body portion 10 are used in place of the switching valve 56, the switching valve drive circuit 55 and the switching control unit 116. Referring to FIG. 1, the cuff 20 is detachably connected to the main body portion 10, as a result of the air tube 31 connected to the cuff 20 being detachably inserted into an insertion opening 10A preformed in a lateral face of the casing of the main body portion 10.

FIG. 13 shows a state in which the state of switching to the cuff 20 side by the aforementioned switching valve 56 is realized by alternatively using the measurement plug 311. Referring to FIG. 13, the air tube 31 joined to the cuff 20 (equivalent to the second air tube 31) is inserted into an opening of the measurement plug 311, which is a hollow cylindrical member, at one end in the longitudinal direction, thereby integrally connecting both parts. By inserting the other opening side of the measurement plug 311 externally into the insertion opening 10A preformed in the lateral face of the casing of the main body portion 10, the air tube 31 (first air tube 31) joined to the internal air system is inserted into the other opening. In this state, the channel of the third air tube 31 joined to the tank 57 is positioned orthogonally to the lateral face extending in the longitudinal direction of the measurement plug 311 by the measurement plug 311 being inserted, causing the channel of the third air tube 31 to be plugged and blocked off by the measurement plug 311. As a result, the second air tube 31 is connectable to the first air tube 31.

FIG. 14 shows a state in which the state of switching to the tank 57 side by the aforementioned switching valve 56 is alternatively realized by the inspection plug 312. Referring to FIG. 14, the insertion opening 10A is completely blocked off, as a result of the inspection plug 312 being inserted externally into the insertion opening 10A preformed in the lateral face of the casing of the main body portion 10. In this state, the inspection plug 312 functions as a plug member for blocking off the second air tube 31, and acts so as to establish an air channel linking the third air tube 31 connected to the tank 57 and the first air tube 31 connected to the air system, in order to inspect for abnormality of the pressure sensor 32.

Figure 15:
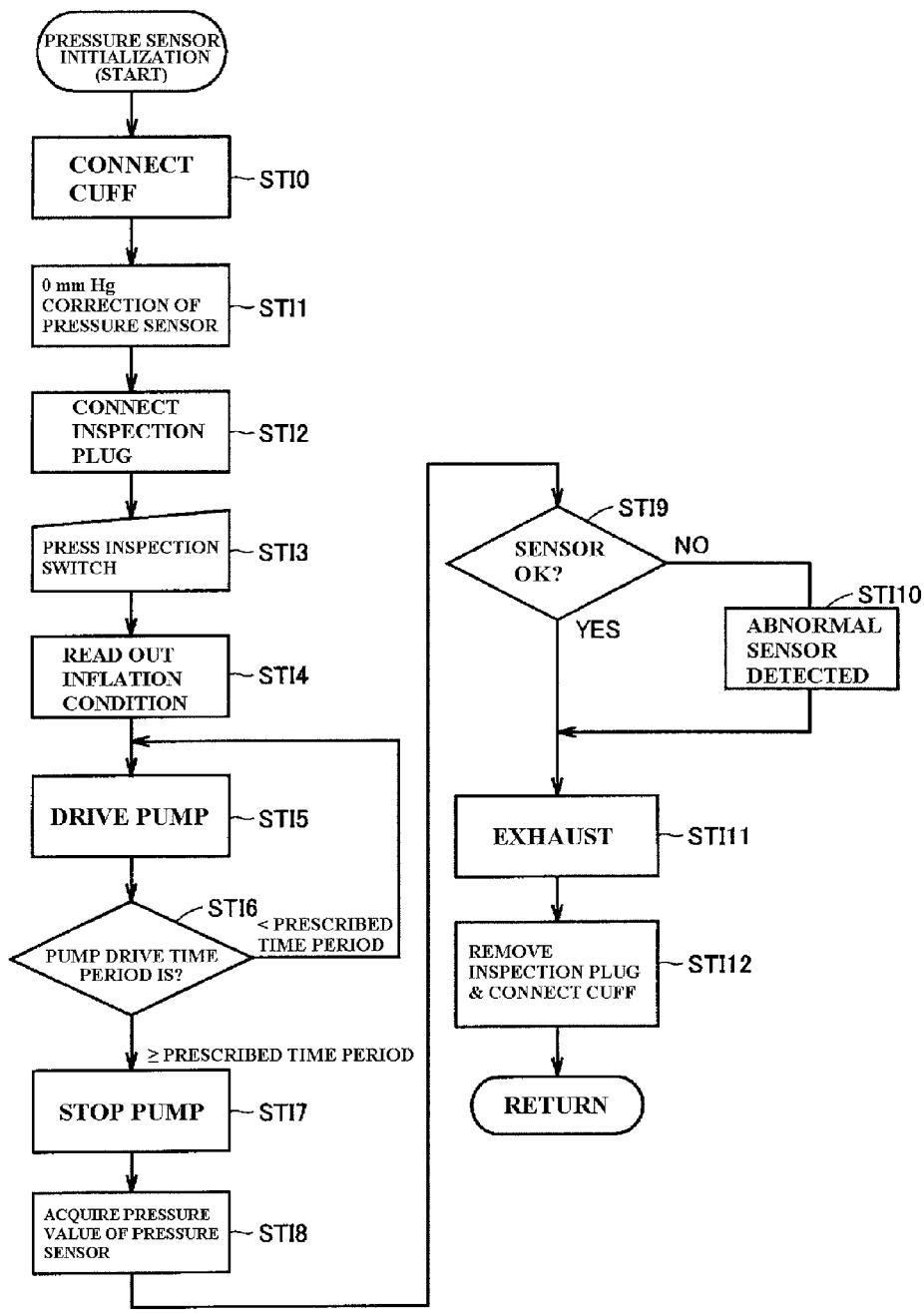
FIG. 15 is another flowchart of pressure sensor abnormality detection processing according to the embodiment.

FIG. 15 shows the procedure of pressure sensor initialization processing (step ST3) using the plugs shown in FIG. 13 and FIG. 14. The other procedures of blood pressure measurement processing apart from the pressure sensor initialization processing are the same as those shown in FIG. 4, and description thereof is omitted. Here, because a trigger for starting inspection needs to be input in the case of using the inspection plug 312, an inspection switch 41F is additionally provided in the operation unit 41. The trigger for starting inspection is input by the person being measured pressing the inspection switch 41F. Alternatively to the inspection switch 41F, the connection of the inspection plug 312 may be detected by a sensor or the like, and a trigger for starting inspection may be input based on the detection signal from the sensor or the like.

First, a user inserts the measurement plug 311 into the insertion opening 10A, as shown in FIG. 13 (step STI0). In this state, 0 mm Hg correction processing of the pressure sensor 32 is performed (step STI1). This 0 mm Hg correction processing is similar to step ST111.

Thereafter, the person being measured removes the measurement plug 311 from the insertion opening 10A, and inserts the inspection plug 312 instead (step STI2). The electronic sphygmomanometer will thereby be in the state shown in FIG. 14. In this state, the person being measured operates the inspection switch 41F (step STI3). The mode of FIG. 14 is thereby achieved, and the configuration for inspecting for abnormality of the pressure sensor 32 is adopted.

The processing of the subsequent steps STI4 to STI11 is the same as the processing of steps ST121 to ST191 in FIG. 11, and description thereof is omitted.

When abnormality detection of the pressure sensor 32 is completed by the above procedure, in step STI12 the person being measured removes the inspection plug 312 from the insertion opening 10A and inserts the measurement plug 311 instead, in order to measure the blood pressure value. The electronic sphygmomanometer 1 will thereby be in the state shown in FIG. 13.

The procedure for abnormality detection of the pressure sensor 32 using the inspection plug 312 is thereby ended.

External Connection of Tank to Main Body Portion 10

In the above description, the tank 57 used for abnormality detection of the pressure sensor 32 was provided in the main body portion 10, but the tank 57 may be connected externally to the main body portion 10.

Figure 16:
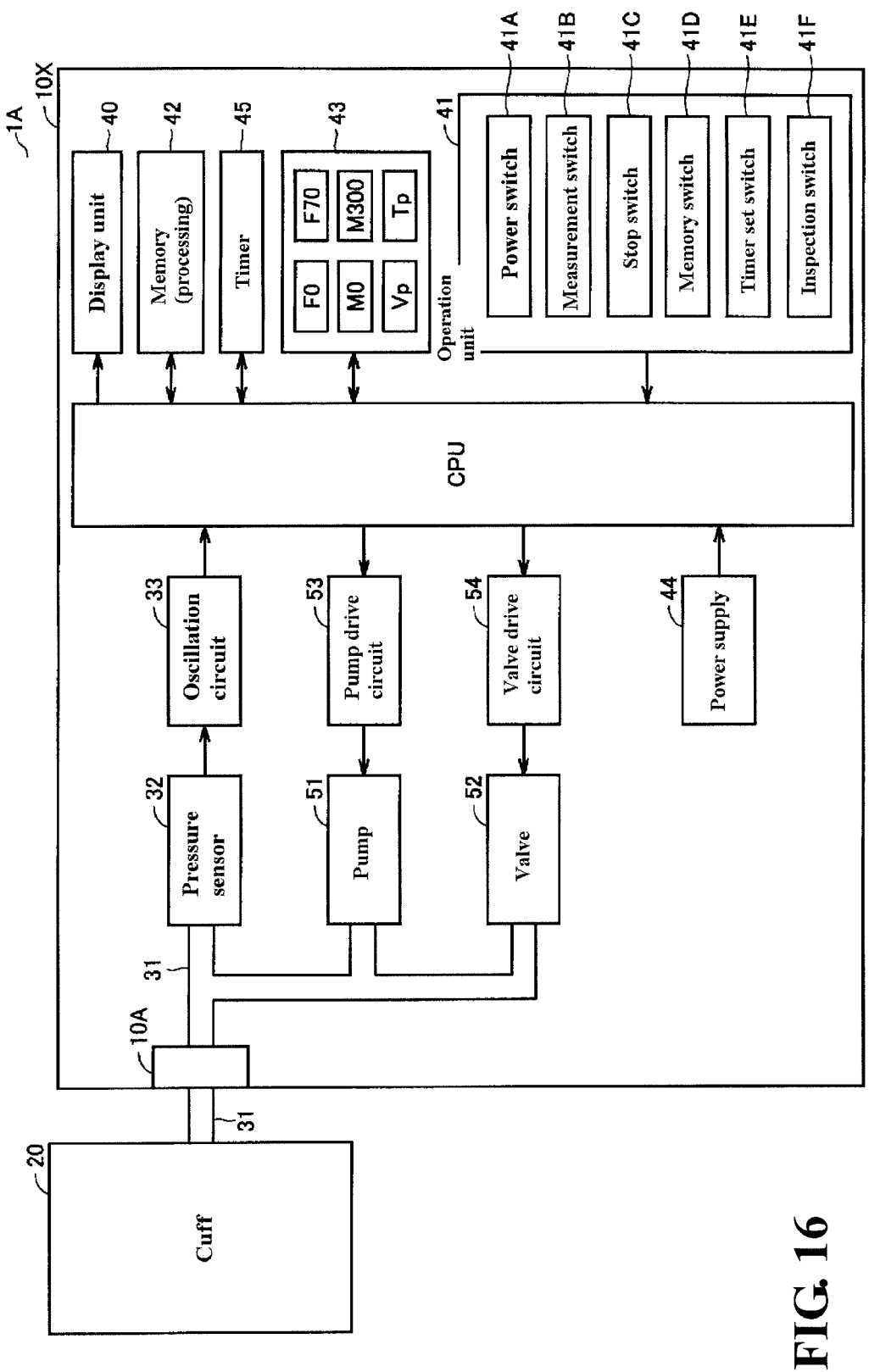
FIG. 16 is a hardware configuration diagram of an electronic sphygmomanometer in which a cuff is externally connected to an insertion opening.
Figure 17:
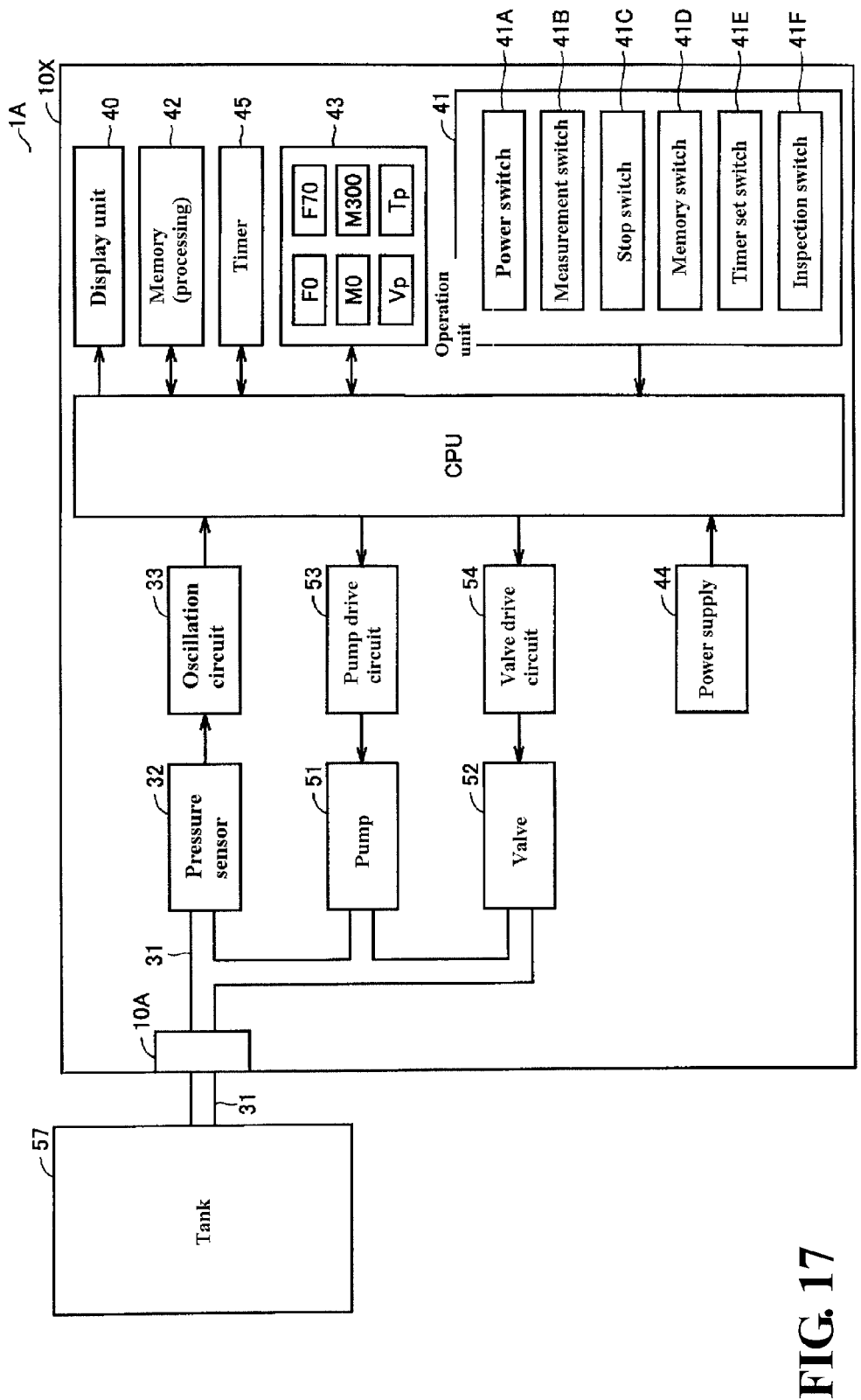
FIG. 17 is a hardware configuration diagram of the electronic sphygmomanometer in which a tank is externally connected to the insertion opening.

A main body portion 10X of an electronic sphygmomanometer 1A is shown in FIG. 16 and FIG. 17. In FIG. 16 and FIG. 17, the switching valve 56, the switching valve drive circuit 55 and the switching control unit 116 are not required as a result of the tank 57 being provided externally to the main body portion. The remaining configuration of the electronic sphygmomanometer 1A is similar to that shown in FIG. 2.

Referring to FIG. 16, the cuff 20 is detachably connected to the main body portion 10X, as a result of the air tube 31 connected to the cuff 20 being detachably inserted into the insertion opening 10A preformed in the lateral face of the casing of the main body portion 10X. In the present embodiment, the tank 57 is inserted into the insertion opening 10A instead of the cuff 20 in the abnormality inspection of the pressure sensor 32 (see FIG. 17), whereas the cuff 20 is inserted into the insertion opening 10A in place of the tank 57 when the inspection has ended or when measuring blood pressure.

Figure 18:
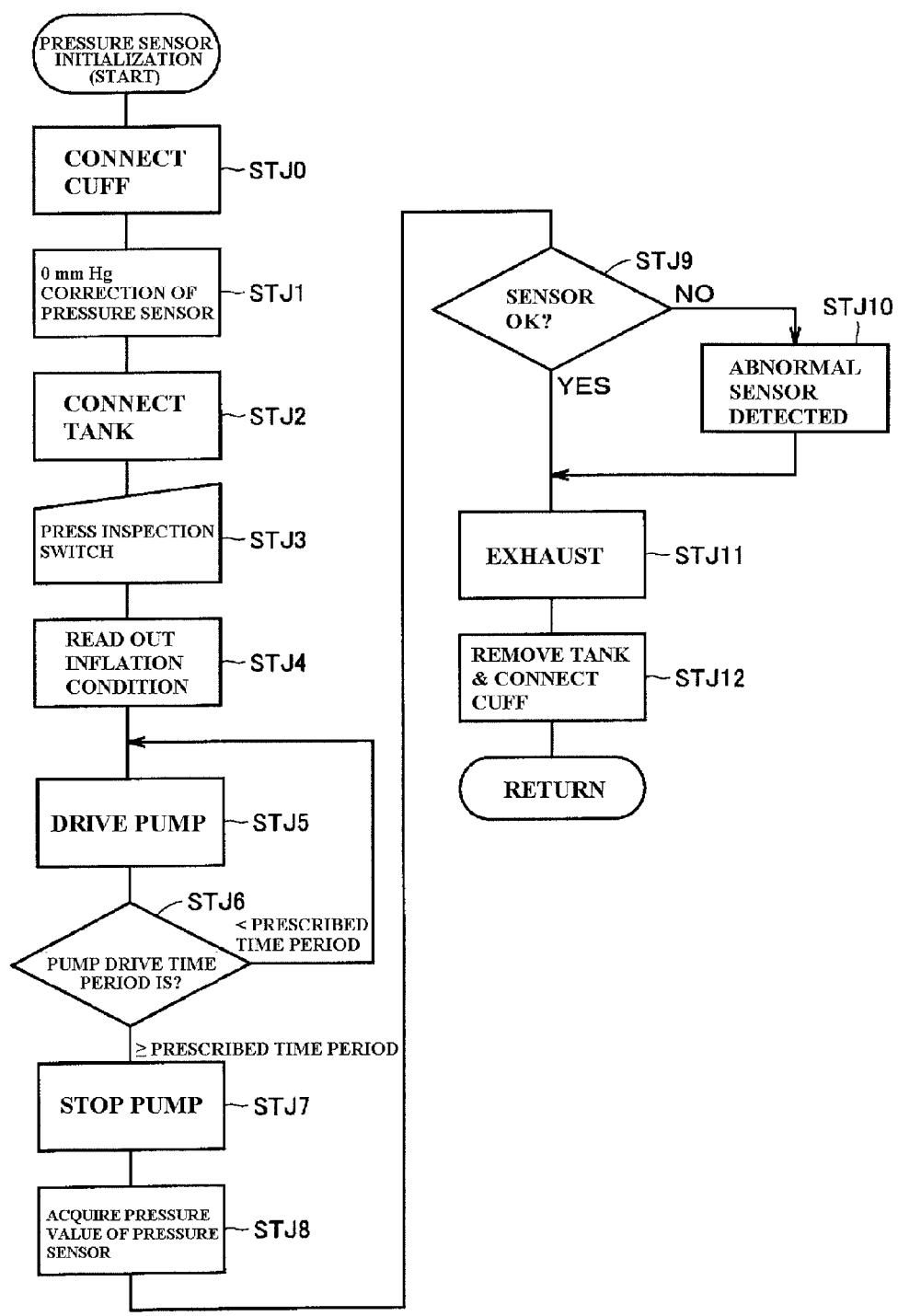
FIG. 18 is a flowchart of pressure sensor abnormality detection processing in the case where either a cuff or a tank is selectively connected externally.

FIG. 18 shows the procedure of pressure sensor initialization processing according to the configuration of FIG. 16 and FIG. 17. This procedure is equivalent to the processing of step ST3 in FIG. 4. The other procedures of blood pressure measurement processing apart from the pressure sensor initialization processing are the same as those shown in FIG. 4, and description thereof is omitted.

Here, because a trigger for starting abnormality inspection needs to be input in the case of using the external tank 57, the inspection switch 41F is added to the operation unit 41. The trigger for starting inspection is input by the person being measured pressing the inspection switch 41F. Alternatively to the inspection switch 41F, the detection signal of a sensor or the like may be used. In other words, external connection of the tank 57 may be detected by a sensor or the like, and a trigger for starting inspection may be input based on the detection signal from the sensor.

First, the user connects the cuff 20 to the insertion opening 10A (step STJ0). In this state, 0 mm Hg correction processing on the pressure sensor 32 is performed (step STJ1). The 0 mm Hg correction processing is similar to step ST111.

Thereafter, the person being measured removes the cuff 20 from the insertion opening 10A, and connects the tank 57 instead (step STJ2). In this state, the person being measured operates the inspection switch 41F (step STJ3). The electronic sphygmomanometer 1A thereby adopts the configuration for inspecting for abnormality of the pressure sensor 32, as shown in FIG. 17.

The processing of the subsequent steps STJ4 to STJ11 is the same as the processing of steps ST121 to ST191 in FIG. 11, and description thereof is omitted. Once abnormality detection of the pressure sensor 32 is completed by the above procedure, in step STJ12 the person being measured removes the tank 57 from the insertion opening 10A, and connects the cuff 20 instead, in order to measure the blood pressure value.

The procedure for abnormality detection of the pressure sensor 32 using the external tank 57 is thereby ended.

Other Embodiments

Figure 19:
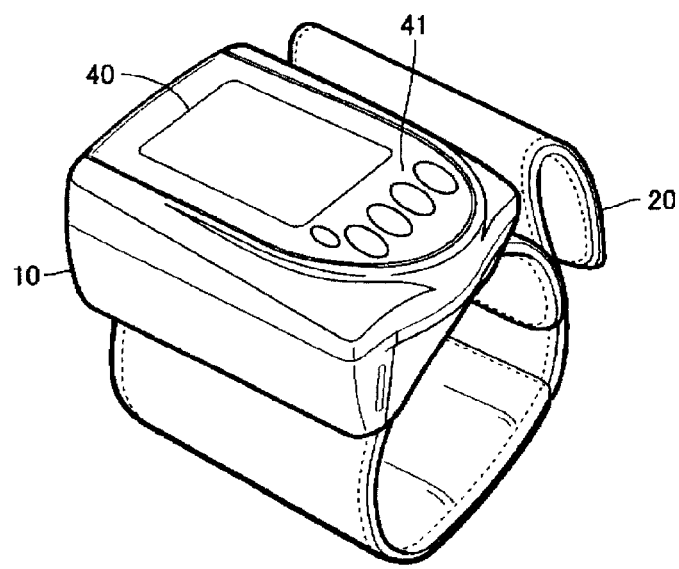
FIG. 19 is a diagram showing the external appearance of a wrist-type electronic sphygmomanometer.

In the abovementioned embodiment, the electronic sphygmomanometer 1 is a floor standing sphygmomanometer configured such that the cuff 20 is wrapped around an upper arm portion, but, as shown in FIG. 19, one or more embodiments of the present invention can be similarly applied to a wrist-type electronic sphygmomanometer in which the cuff 20 and the main body portion 10 are integrally constituted, and the cuff 20 is wrapped around the wrist.

In the abovementioned embodiment, processing for initializing the pressure sensor 32 including processing for detecting abnormality of the pressure sensor 32 may be carried out directly after operation of the power switch 41A is detected (step ST1) and before the initialization processing (step ST2). Alternatively, the initialization may be carried out directly after the measurement switch 41B is operated (step ST4).

Although the data in (A) and (B) of FIG. 5 is assumed to be stored in the internal memory 43, this data may be stored in an unshown external memory.

The processing for detecting abnormality of the pressure sensor 32 may be performed at a prescribed time interval, or may be performed whenever blood pressure measurement is performed a prescribed number of times. Alternatively, a configuration may be adopted in which abnormality detection is performed when the person being measured inputs an inspection instruction from outside, without determining the interval.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

REFERENCE NUMERALS LIST 1 electronic sphygmomanometer
55 switching valve drive circuit
56 switching valve
57 tank
32 pressure sensor
33 oscillation circuit
112 blood pressure calculating unit
113 sensor abnormality detector
311 measurement plug
312 inspection plug

The invention claimed is:

1. An electronic sphygmomanometer comprising:
a cuff to be mounted on a measurement site;
a tank that stores a prescribed amount of fluid;
a pressure adjusting unit that adjusts pressurization of the cuff or the tank, by supplying or discharging the fluid;
a pressure detector comprising a pressure sensor, the pressure detector detecting a pressure in the cuff and a pressure in the tank based on pressure information output from the pressure sensor, wherein the pressure detector selectively detects the cuff pressure or the tank pressure based on a switching signal;
a blood pressure calculating unit that calculates a blood pressure value based on a change in the pressure in the cuff detected by the pressure detector;
an abnormality detector that detects whether the pressure sensor is abnormal; and
a first channel through to the pressure adjusting unit and the pressure detector, and comprising one of the tank and the cuff selectively connected thereto,
wherein the abnormality detector detects whether the pressure sensor is abnormal, based on the pressure in the tank detected by the pressure detector in accordance with the pressure information output from the pressure sensor, in a state where the tank is connected to the first channel and the fluid is supplied to the connected tank.

2. The electronic sphygmomanometer according to claim 1, further comprising:
a second channel through to the cuff; and
a third channel through to the tank,
wherein the abnormality detector comprises a channel switching unit that selectively connects one of the second channel and the third channel to the first channel, and
wherein the channel switching unit comprises a switching valve that connects one of the second channel and the third channel to the first channel, in accordance with a provided switching signal.

3. The electronic sphygmomanometer according to claim 2,
wherein the channel switching unit comprises a connecting portion that detachably connects the second channel to a main body of the electronic sphygmomanometer, and a plug member that blocks off the second channel,
wherein the second channel through to the cuff integrally comprises the connecting portion, and wherein the connecting portion is a hollow cylinder, with the second channel being connected to the first channel as a result of the connecting portion being mounted on the main body such that the cylinder is inserted into the first channel and the third channel is blocked off by the inserted cylinder, and the third channel being connected to the first channel as a result of the plug member being mounted on the main body in place of the connecting portion.

4. The electronic sphygmomanometer according to claim 2,
wherein the pressure adjusting unit comprises a pump that sends the fluid at a fixed flow rate per unit time, and supplies the prescribed amount of the fluid to the tank by driving the pump for a fixed time period.

5. The electronic sphygmomanometer according to claim 2, further comprising a temperature detector that detects an ambient temperature of the tank,
wherein the prescribed amount of the fluid is changed in accordance with the temperature detected by the temperature detector.

6. The electronic sphygmomanometer according to claim 2,
wherein a result of detection by the abnormality detector is output externally.

7. The electronic sphygmomanometer according to claim 2, further comprising a storage unit,
wherein a result of detection by the abnormality detector is stored in the storage unit in association with data indicating the blood pressure value calculated by the blood pressure calculating unit and a time at which the blood pressure value was calculated.

8. The electronic sphygmomanometer according to claim 1,
wherein the abnormality detector detects whether the pressure sensor is abnormal, at a time of starting the electronic sphygmomanometer.

9. The electronic sphygmomanometer according to claim 1,
wherein the abnormality detector detects whether the pressure sensor is abnormal, at a time of calculating the blood pressure value by the blood pressure calculating unit.

10. The electronic sphygmomanometer according to claim 1,
wherein the abnormality detector detects whether the pressure sensor is abnormal once after an elapse of a predetermined period of time.

11. The electronic sphygmomanometer according to claim 1,
wherein the abnormality detector detects whether the pressure sensor is abnormal once after a predetermined number of times of the blood pressure value calculations are performed.

12. The electronic sphygmomanometer according to claim 1, wherein the abnormality detector detects whether the pressure sensor is abnormal in response to an instruction externally provided to the electronic sphygmomanometer.

* * * * *